United States Patent
Herron

(12) 
(10) Patent No.: US 6,906,237 B2
(45) Date of Patent: Jun. 14, 2005

(54) VIVO ASSAY FOR ANTI ANGIOGENIC COMPOUNDS

(76) Inventor: G. Scott Herron, P.O. Box 353, La Honda, CA (US) 94020

( * ) Notice: Subject to any disclaimer, the term of this patent is extended or adjusted under 35 U.S.C. 154(b) by 394 days.

(21) Appl. No.: 09/905,704

(22) Filed: Feb. 27, 2001

(65) Prior Publication Data

US 2003/0170889 A1 Sep. 11, 2003

Related U.S. Application Data

(60) Provisional application No. 60/271,778, filed on Feb. 27, 2001.

(51) Int. Cl.$^7$ .................. A01K 67/00; A01K 67/33; G01N 33/00
(52) U.S. Cl. .................. 800/8; 800/3
(58) Field of Search .................. 800/3, 8; 435/325, 435/41; 424/9.1, 9.2; 935/41

(56) References Cited

U.S. PATENT DOCUMENTS 5,602,305 A * 2/1997 Pober et al. .................. 800/11
6,166,178 A    12/2000 Cech et al. .................. 530/324

FOREIGN PATENT DOCUMENTS

WO    WO 9924565 A1 * 5/1999 .......... C12N/15/12
WO    WO 00/56898       9/2000

OTHER PUBLICATIONS

Thomas,Jan. 2000, Nature Biotech. vol. 18, pp. 39–42.*
Yang,1999, Jour. Biol. Chem., vol. 274, pp. 26141–26148.*
Okabe, 1997, FEBS Letters, vol. 407, 313–319.*
Bunk,2001,The Scientist, vol. 15, p. 21.*
Prewett,1999, Cancer Research, vol. 59, pp. 5209–5218.*
Ueno,1997, Arter.Thromb. Vasc. Biol., vol. 17, pp. 2453–2460.*
Yang, T. (2001). "Telomerized Human Microvasculature Is Functional In Vivo," *Nature Biotechnology* 19:219–224.

* cited by examiner

*Primary Examiner*—Michael Wilson
*Assistant Examiner*—Valarie Bertoglio
(74) *Attorney, Agent, or Firm*—Fenwick & West LLP

(57) ABSTRACT

We report the use of telomerase-immortalized human microvascular endothelial cells in the formation of functional capillary blood vessels in vivo. Previously we showed the superior in vitro survival of human telomerase reverse transcriptase (hTERT)-transduced human endothelial cells. Here we show that retroviral-mediated transduction of hTERT in human dermal microvascular endothelial cells (HDMEC) results in cell lines that form microvascular structures when subcutaneously implanted in severe combined immunodeficiency (SCID) mice. The human origin of xenografted microvaculature was confirmed both by basement membrane immunoreactivity with anti-human type IV collagen staining and visualization of fluorescent vessels containing HDMEC that were co-transduced with hTERT and green fluorescent protein (eGFP). The lack of human vascular structures after implantation of HT1080 fibrosarcoma cells, 293 human embryonic kidney cells or human skin fibroblasts demonstrated the specificity of HDMEC at forming capillaries. Intravascular red fluorescent microspheres injected into the host circulation were found within green "telomerized" microvessels indicating functional murine-human vessel anastamoses. Whereas primary HDMEC-derived vessel density decreased steadily with time, telomerized HDMEC maintained durable vessels 6 weeks after xenografting. Modulation of implant vessel density by exposure to different angiogenic and angiostatic factors demonstrated the utility of this system for the study of human microvascular remodeling in vivo.

28 Claims, 5 Drawing Sheets

VIVO ASSAY FOR ANTI ANGIOGENIC COMPOUNDS

This application claims priority under 35 U.S.C 119(e) from U.S. Provisional Application Ser. No. 60/271,778, filed Feb. 27, 2001.

FIELD OF THE INVENTION

The present invention relates to assays and kits for screening compounds to identify modulators of angiogenesis. In particular, an assay for rapidly screening compounds that modulate angiogenesis is provided.

BACKGROUND OF THE INVENTION

Cell proliferation and survival are critical parameters useful for screening compounds for treatment of various disorders, including tumors and other proliferative disorders. Compounds that are selected for their ability to inhibit cell proliferation can act to (1) inhibit mitogenesis, (2) inhibit angiogenesis, or (3) activate the complement pathway and the associated killer cells.

Angiogenesis is normally observed in wound healing, fetal and embryonal development and formation of the corpus luteum, endometrium and placenta. The control of angiogenesis is a highly regulated system of angiogenic stimulators and inhibitors. Thus, angiogenesis is a critical component of the body's normal physiology, especially during wound healing.

In addition, the control of angiogenesis has been found to be altered in certain disease states, and, in many cases, the pathological damage associated with the disease is related to the uncontrolled angiogenesis. It also has a detrimental aspect, for example, when blood vessels multiply and enhance growth and metastasis of tumors. Aberrant angiogenesis is also associated with numerous disorders, including rheumatoid arthritis, where blood vessels invade the joint and destroy cartilage, and numerous ophthalmologic pathologies, such as diabetic retinopathies in which new capillaries invade the vitreous, bleed and cause blindness, and macular degeneration, prostate cancer and Kaposi's carcinoma. Angiogenesis is essential to tumor development and growth. Prevention of angiogenesis can inhibit solid tumor growth.

Compounds that have anti-angiogenic activity can be used, for example, as anti-tumor agents and for the treatment of ophthalmic disorders, particularly involving the retina and vitreous humor, and for hyperproliferative dermatological disorders, such as psoriasis, that have an angiogenic component. Thus, compounds that enhance angiogenesis and compounds that inhibit angiogenesis are being sought.

This has led to a search for specific inhibitors of endothelial cell growth. As a result, there is an interest in measuring proliferation of endothelial cells under inhibitory and stimulatory conditions as screens for discovery of inhibitors (or alternatively stimulators) of angiogenesis. Direct assessment of cell numbers, either microscopically or by particle counter is time consuming and not amenable for high throughput screening. Consequently, direct assessment has been replaced by indirect methods, such as by packed cell volume, by chemical determination of a cellular component, for example, protein or deoxyribonucleic acid, or by uptake of a chromogenic dye such as neutral red. These methods can be laborious when handling large numbers of cultures, and also inaccurate at low cell densities. For high throughput screening protocols it is necessary to rapidly and accurately measure low cell densities and/or relatively small changes in cell number over a large range of cell densities. Presently available protocols to not provide a means to do this and do not measure the end result of angiogenesis which is a change in the number of capillary blood vessels. Thus, there is a need for convenient, rapid and reproducible assays for identifying agents that modulate angiogenesis as well as agents that modulate cell proliferation.

Therefore it is an object herein to provide a method for identifying compounds that modulate both endothelial cell proliferation and changes in the number of microvascular structures in a given volume of tissue. In particular, it is an object herein to provide a method for screening for modulators of angiogenesis, particularly inhibitors thereof.

SUMMARY OF THE INVENTION

In order to meet these needs, the present invention is directed to an in vivo method for identifying anti-angiogenic compounds that modulate cell proliferation and/or changes in the number of microvascular structures. In particular, the present invention is directed to an in vivo method for screening for modulators of angiogenesis, particularly inhibitors thereof by monitoring the appearance of microvascular tubular structures.

DETAILED DESCRIPTION OF THE INVENTION

Figure 1:
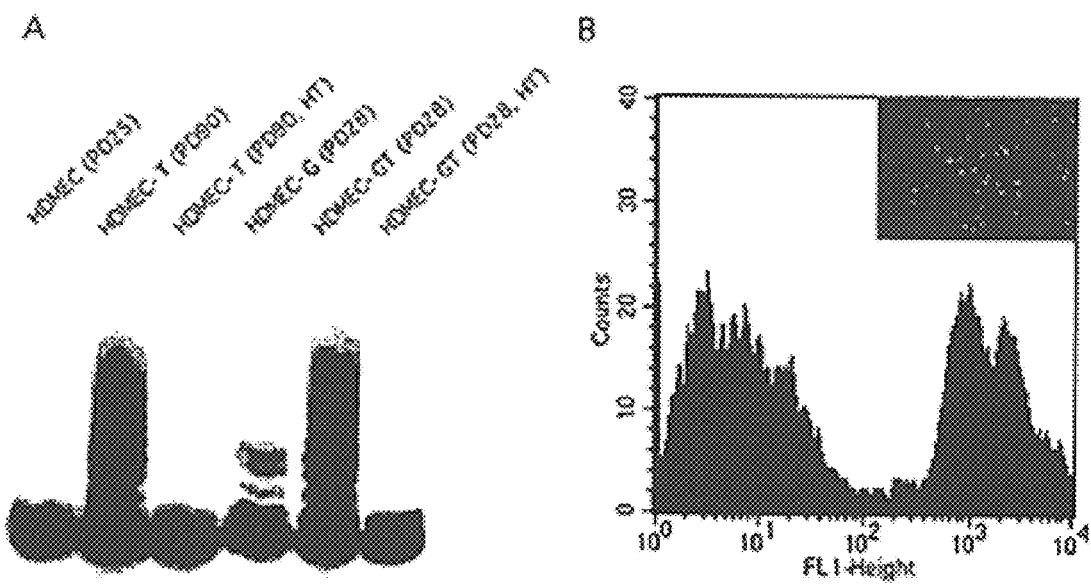
FIG. 1 shows the characterization of telomerase activity and fluoresence signal of eGFP-labeled primary HDMEC and telomerized cells. (A) Telomerase activity by TRAP protocol in two different primary parental HDMEC (non-eGFP labeled HDMEC, eGFP-labeled HDMEC-G) and their telomerized progeny (HDMEC-T, HDMEC-GT). Telomerized cells showed typical 6-nucleotide-DNA laddering at PD90 and PD28, respectively, whereas, little or no activity was observed in parental controls at PD25 and PD28. No TRAP activity was present in heat treated (HT, 65° C.×10 min) samples. (B) HDMEC-GT was sorted into a GFP(+) subpopulation by FACS. Two peaks in the GFP(+) population indicate some variability of fluorescence intensity among cells (insert). FAC-sorted HDMEC-GT maintained similar fluoresence signal patterns at PD80.

The practice of the present invention will employ, unless otherwise indicated, conventional methods of molecular biology, chemistry, biochemistry and pharmacology, within the skill of the art. Such techniques are explained fully in the literature. See, e.g., *Remington's Pharmaceutical Sciences*, 19th Edition (Easton, Pa.: Mack Publishing Company, 1995); *Methods In Enzymology* (S. Colowick and N. Kaplan, eds., Academic Press, Inc.); Wang, A. M., et al. in *PCR Protocols: a Guide to Methods and Applications* (M. A. Innis, et al., eds.) Academic Press (1990); Kawasaki, E. S., et al., in *PCR Technology: Principles and Applications of DNA Amplification* (H. A. Erlich, ed.) Stockton Press (1989); Hochuli, E., in *Genetic Engineering, Principals and Practice, Vol.* 12 (J. Stelow Ed.) Plenum, N.Y., pp. 87–98 (1990); Ausubel, F. M., et al., *Current Protocols in Molecular Biology*, John Wiley and Sons, Inc., Media Pa.; and, Sambrook, J., "Nucleic acid expression vector" or "Expression cassette" refers to an assembly which is capable of directing the expression of a sequence or gene of interest. The nucleic acid expression vector includes a promoter which is operably linked to the sequences or gene(s) of interest. Other control elements may be present as well. Expression cassettes described herein may be contained within, for example, a plasmid or viral vector construct. In addition to the components of the expression cassette, the plasmid construct may also include a bacterial origin of replication, one or more selectable markers, a signal which allows the plasmid construct to exist as single-stranded DNA (e.g., a M13 origin of replication), a multiple cloning site, and a "mammalian" origin of replication (e.g., a SV40 or adenovirus origin of replication).

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys anntroduce one or more exogenous DNA moieties into suitable host cells. The term refers to both stable and transient uptake of the genetic material, and includes uptake of peptide- or antibody-linked DNAs.

A "vector" is capable of transferring gene sequences to target cells (e.g., viral vectors, non-viral vectors, particulate carriers, and liposomes). Typically, "vector construct," "expression vector," and "gene transfer vector," mean any nucleic acid construct capable of directing the expression of a gene of interest and which can transfer gene sequences to target cells. Thus, the term includes cloning and expression vehicles, as well as viral vectors.

A "selectable marker" or "reporter marker" refers to a nucleotide sequence included in a gene transfer vector that has no therapeutic activity, but rather is included to allow for simpler preparation, manufacturing, characterization or testing of the gene transfer vector.

By "pharmaceutically acceptable" or "pharmacologically acceptable" is meant a material which is not biologically or otherwise undesirable, i.e., the material may be administered to an individual in a formulation or composition without causing any undesirable biological effects or interacting in a deleterious manner with any of the components of the composition in which it is contained.

By "antiangiogenic" compound it is meant a compound that inhibits angiogenisis. Such compounds may be organic or inorganic. Organic compounds include peptides and cDNAs encoding such peptides. Such compounds further include synthetic compounds, natural products, traditional medicine based and genetically engineered bioactive agents.

Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

The endostatin-HEK293 data we describe in detail below, represents an experimental concept that can be modified in a variety of ways to provide a high throughput screen (HTS) of antiangiogenic compounds for their effects on human endothelial cells by monitoring the appearance of microvascular tubular structures.

A. In vitro Scale-up

Co-plate into "permissive" matrices (e.g. Matrigel, collagen, reconstituted basement membrane, synthetic dermal equivalents, etc.), in a microtiter well format, telomerized-fluorescently labeled human dermal microvascular endothelial cells (TMEC) together with a "bioreactor" cell type (e.g. HEK293 cells) that expresses a gene of interest. Readout would be vessel density as measured by a robotic, inverted fluorescent microscope (e.g. Gen-2, made by Universal Imaging, Inc., powered by customized MetaMorph vascular tracing software that utilizes digitizing algorithms like the MossFilter, created by W. C. Moss, as presented in detail below). Control wells representing maximum and minimum vascularization values would be included on each plate for baseline limits.

Variation of this basic method includes antiangiogenic agents including genes other than endostatin and compounds affecting vessel formation that may or may not be related to the gene being expressed. Thus, if a research program is investigating a specific gene and has a number of synthetic peptides (generated by bioinformatic molecular modeling programs) and/or immunoreagents that antagonize or mimic the effects of the gene product, the co-plating is performed in the presence of different concentrations of the compound. Examples of specific genes that could be tested include growth factors and their specific binding domains (FGF-2, EGF, VEGF1,2,3,4, PDGF, IGF, TGF, PLGF, SF, angiopoietins, CTGF), extracellular matrix molecules and their binding domains (fibronectin, vitronectin, collagens 1, 3, 4, 8, 18, laminins 1, 5, 8, entactin, thrombospondins, fibrillins, proteoglycans), proteinase inhibitors (TIMPs, alpha1 macroglobulin, antiproteinases), cell adhesion molecules and their binding domains (PECAM, ICAM, VCAM, E-selectin, CD34, CD36, CD43, beta1,3, 5 integrins), known angiostatic genes (endostatin, angiostatin) and apoptotic inducers (TNF, fas), inflammatory mediators (interleukins, bradykinins, neuropeptides, histamines, chemokines). Compounds that can be tested include icosinoids, retinoids, vitamin D analogues, fumagillins, nitric oxides, etc.

The genetic material expressed by the bioreactor cell can derived in two ways: a) random approach; b) intelligent approach. The former approach utilizes a shotgun transfection, retroviral or other gene transduction method to express 200–500 genes in a population of bioreactor cells. The genes to be shotgun expressed in this manner may be derived from commercial sources (e.g. cDNA libraries from Clontech/BD, Strategene, Gibco/BRL, ATCC, etc) or from custom libraries provided by the user. The type of bioreactor cell can be varied. As explained in detail below, we initially used HEK293 cells because we found that they did not form tubular structures in our Matrigel implants in vivo (thus not confounding the assay) nor form large tumors but remained as small colonies and nests of cells that expressed the transgene of interest. The system clearly can be used to test other tumor cell types to determine if gene targeting to the tumor cell of interest can affect new vessel growth, thus supporting the use of that gene for ectopic expression in vivo. For physiologic studies (e.g. wound repair) or pathologic studies not involving tumor angiogenesis (e.g. psoriasis, atherosclerosis, diabetic retinopathy, chronic ulcers) a cell type found anatomically related to the microvasculature (e.g. pericytes, smooth muscle cells, adventitial or dermal fibroblasts, dendritic cells, etc.) could be transduced with the gene of interest and co-plated or co-cultured with TGMEC and the same read-out performed.

To screen genes using the intelligent approach, companies that have already generated libraries of bioactive genes by proprietary methods (e.g. Rigel, Exelexis, Genentech, Human Genome Sciences, Millenium, AmGen, Incyte, Celomics, Hyseq, Axys, etc) may select less than 100 genes at a time to express in the bioreactor cell. Some of these companies have custom libraries that were generated by screening for their effects on endothelial cell physiologic processes (e.g. migration, cytoskeletal changes, integrin or other adhesion molecule expression, tubule formation, cytotoxicity, etc). Alternative methods of intelligent gene screening involve constructing chimeric genes containing resistance factors that allow selection pressure to be applied (e.g. hygromycin, ampicillin, etc) or inducible marker expression (tet-inducer, tamoxifen, metallothionine, etc) that will allow detection of gene of interest in the presence of the selection agent or inducer.

B. In vivo

Genes and compounds already screened by the above methods are then validated for their effects in vivo using SCIDS. The latter system itself can be scaled-up by implanting up to 4 grafts per mouse using surgical templates and graft harvesting techniques. This second round of screening integrates with the first by its use of the same cell types and same genes but elevates the level of functional significance to the order of preclinical selection.

C. In vitro Multiparameter Screens that Map the Angiogenic Program

Assay systems that span specific aspects of the angiogenic cellular differentiation program, each reporting 2–3 key variables (e.g. gene expression, cell signaling, physiologic events [e.g. MMP activity, changes in cell shape, transmigration of subcellular organelles or proteins], morphometric events [e.g. cell migration, tubulogenesis, lumen formation, branching, pruning] or apoptosis, etc.) are utilized. The telomerized cell lines are required for their replicative uniformity, phenotypic expression patterns and functional characteristics. For example: A TGMEC clone is created that expresses a chimeric gene product representing a fused reporter fluorescent gene (NFP)—DNA promoter construct. A gene product (e.g. avb3 vitronectin receptor or Tie-2 Angiopoietin receptor, etc) that only is expressed during the early phase of the angiogenic program will thus monitor only this specific portion of endothelial cell differentiation. These EC lines are engineered to include key read-out indicators to monitor steps in the angiogenic/angiostatic differentiation program. An automated platform that simultaneously measures time courses and endpoints (e.g. light and fluorescence microscopy that uses microtiter plates such as the Gen-2 from Universal Imaging) could run 1–100 plates/day; HTS could screen 50–1000 compounds/day/machine and thus could be scaled-up to thousands of compounds/day (robotics required).

Ultra-HTS could be achieved by designing assays based on intensity data alone without imaging analysis. This comes after proof of principle is achieved by demonstrating that activation of specific genes, signaling pathways and subcellular events which creates the fluorescent "hit" mimics that part of the angiogenic program of interest and commits the system to an angiogenic response.

Although a number of methods and materials similar or equivalent to those described herein can be used in the practice of the present invention, the preferred materials and methods are described herein.

HDMEC Isolation and Culture

The establishment of primary HDMEC was performed by dispase digestion of neonatal foreskin tissue and EC purification using anti-PCAM-1 affinity beads as described[38,39]. The references cited herein are described in detail at the end of the description. Primary HDMEC and telomerized EC (HDMEC-T) were cultured in EGM-2-MV medium (Clonetics, San Diego, Calif.). Medium was changed every two days and cells were passaged 1:3. Two primary parental HDMEC populations used in this study were designated HDMEC-1 and HDMEC-G. The latter cells were created by transduction of early passage (PD5) HDMEC with the LZRS retroviral vector expressing eGFP (kindly provided by Helen Deng, Stanford University, CA) as described below.

Preparation of Telomerized HDMEC Plasmid pGRN145 encoding hTERT was provided by Geron Corporation (Menlo Park, Calif.). The hTERT coding region of pGRN145 was subcloned into the LZRS retroviral vector [Romero, L. I., Zhang, D. N., Herron, G. S. & Karasek, M. A. Interleukin-1 induces major phenotypic changes in human skin microvascular endothelial cells. *J. Cellular Physiol.* 173, 84–92 (1997)] provided by Garry Nolan (Stanford, Calif.). hTERT-LZRS and eGFP-LZRS retroviral particles were produced in the Phoenix packaging cell line (Garry Nolan, Stanford University, Calif.) and both genes were driven by Moloney murine leukemia virus 5'-LTR promoter. Two different HDMEC-T lines were used in this study, HDMEC-T and HDMEC-GT, corresponding to primary parental cell populations, HDMEC-1 and HDMEC-G, respectively. The preparation and characterization of HDMEC-T (aka, hTERT3) was as previously published[21]. An eGFP-labeled telomerized EC population was produced as follows: $1 \times 10^6$ HDMEC at population doubling 5 (PD5), were transduced with hTERT-LZRS, allowed to grow without selection for two passages and then sorted for green fluorescence using a BD FACStar to produce HDMEC-GT. HDMEC-T and HDMEC-GT came from two different primary HDMEC and were phenotypically and functionally similar to young primary cells[21]. HDMEC and HDMEC-G had low wild type p16 expression and exogenous hTERT gene transduction did not affect the pattern of its expression. We did not find c-myc activation in any HDMEC-T used in this report and all HDMEC-T were diploid 46, XY.

Assay for telomerase activity

Telomerase activity was measured by the TRAP kit from Roche Molecular Biochemicals (Indianapolis, Ind.). Briefly, 2000 cell equivalents were PCR-amplified with a biotin-labeled P1-TS primer. One tenth of the PCR product was run on a 12% non-denaturing acrylamide gel. Following gel electrophoresis, products were transferred and blotted onto a nylon membrane, and processed by the biotin luminescence detection kit (Pharmingen, San Diego, Calif.).

3D in vitro Tubule Formation Assay $1 \times 10^4$ HDMEC-G or HDMEC-GT were mixed with 0.5 ml Matrigel (Beckton Dickinson, Bedford, Mass.) on ice and seeded in each well of a 24 well cluster plate. Plates were imaged one week after seeding by both phase contrast and fluorescence microscopy, images were captured using a CCD camera mounted on a Zeiss Inverted microscope and digitally converted using NIH Image.

SCID Mice Xenografting

This procedure is based on a modification of the mouse angiogenesis model previously described[41]. Two-three week old male or female SCID mice (Taconic, Germantown, N.Y.) were used as hosts for all implants. Primary HDMEC and HDMEC-T were harvested, washed twice and re-suspended in serum-free EGM-2 basal medium at the concentration of $1 \times 10^5/\mu l$. Ten $\mu l$ of cells were mixed with 0.5 ml of Matrigel on ice and the mixture was implanted in the ventral midline thoracic tissue of each mouse by subcutaneous injection using a #25 needle. Up to three separate injections could be performed on a single mouse. For some experiments, recombinant human $VEGF_{165}$ (2 $\mu g/ml$) (R&D systems, Minneapolis, Minn.) or bovine FGF-2 (150 ng/ml) (R&D systems, Minneapolis, Minn.) were added to the mixture. When tumor cells (HT1080 and 293, ATCC) or primary human dermal fibroblasts[38] were injected, the procedure remained the same except basal D-MEM medium replaced EGM-2.

Thick Section, Whole Mount Tissue Examination

Whole mount Matrigel implants were examined by fluoresence microscopy as follows: The implants were surgically removed from mice after euthanasia by $CO_2$ asphyxiation, cut into small pieces with a #15 scalpel and further dissected with forceps. Tissues were covered in DABCO mounting medium (Sigma, St. Louis, Mo.) and eGFP signals were captured using the FITC filter on a Zeiss Axioskope microscope equipped with a MC-80 CCD camera. Images were viewed using Adobe Photoshop on a Macintosh Quadra and quantified as described below.

Histology and Human Vessel Quantification

Figure 3:
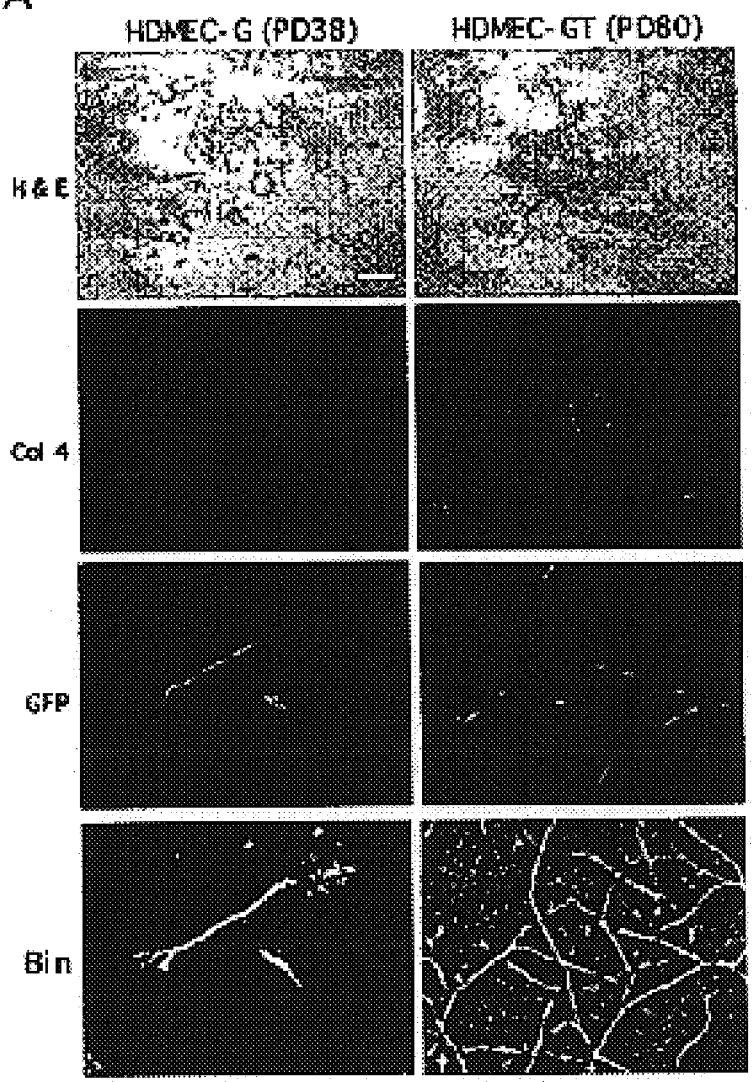
FIG. 3 shows the in vivo tubule formation in SCID mice xenografted with HDMEC. (A) H&E staining, human type IV collagen immunofluorescence and GFP fluorescence signals in sections of Matrigel implants containing pre-senescent HDMEC-G (PD38) and HDMEC-GT (PD80) at two weeks after xenografting. Presence of vascular structures in both primary and telomerized implants is evident in H&E sections; however, only HDMEC-GT formed abundant capillary networks that were immunoreactive with anti-human type IV collagen IgG (col 4) and brightly GFP(+). Details of fluorescent vascular structures are enhanced by digital image analysis using the Moss Filter™ (Bin). Bar: ~20 µm. (B). Graphic representation of human vessel density in Matrigel implants in vivo as a function of time after implantation using micromorphometry (i.e., counting the number of human type IV collagen immunoreactive annular structures per 5 random high power fields). HDMEC-GT at PD54 were directly compared with parental HDMEC-G cells at early (E; PD12), middle (M; PD20) and late (L; PD40) passages. Animals with replicate implants of each cell type were examined at 2 wk (black bars), 4 wk (white bars) and 6 wk (hatched bars) after implantation except for HDMEC-G at E passage, which had only a 2 week time point. The number of HDMEC-GT vessels was significantly different from HDMEC-G at M (*, p<0.01) and L passage (**, p<0.001). Averages and standard deviations are presented and each time point came from at least 3 independent experiments.
Figure 3:
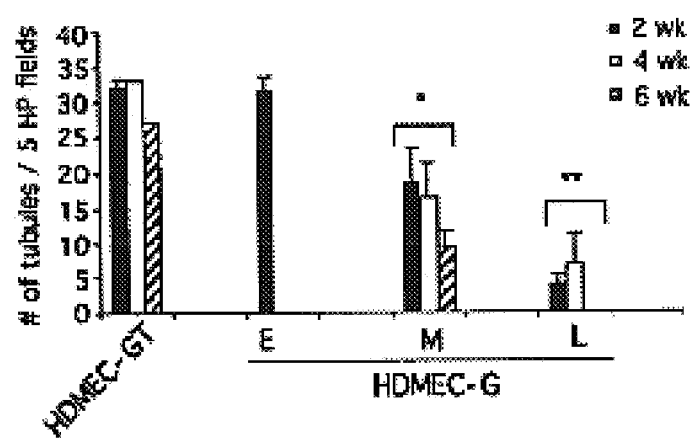
Figure 6:
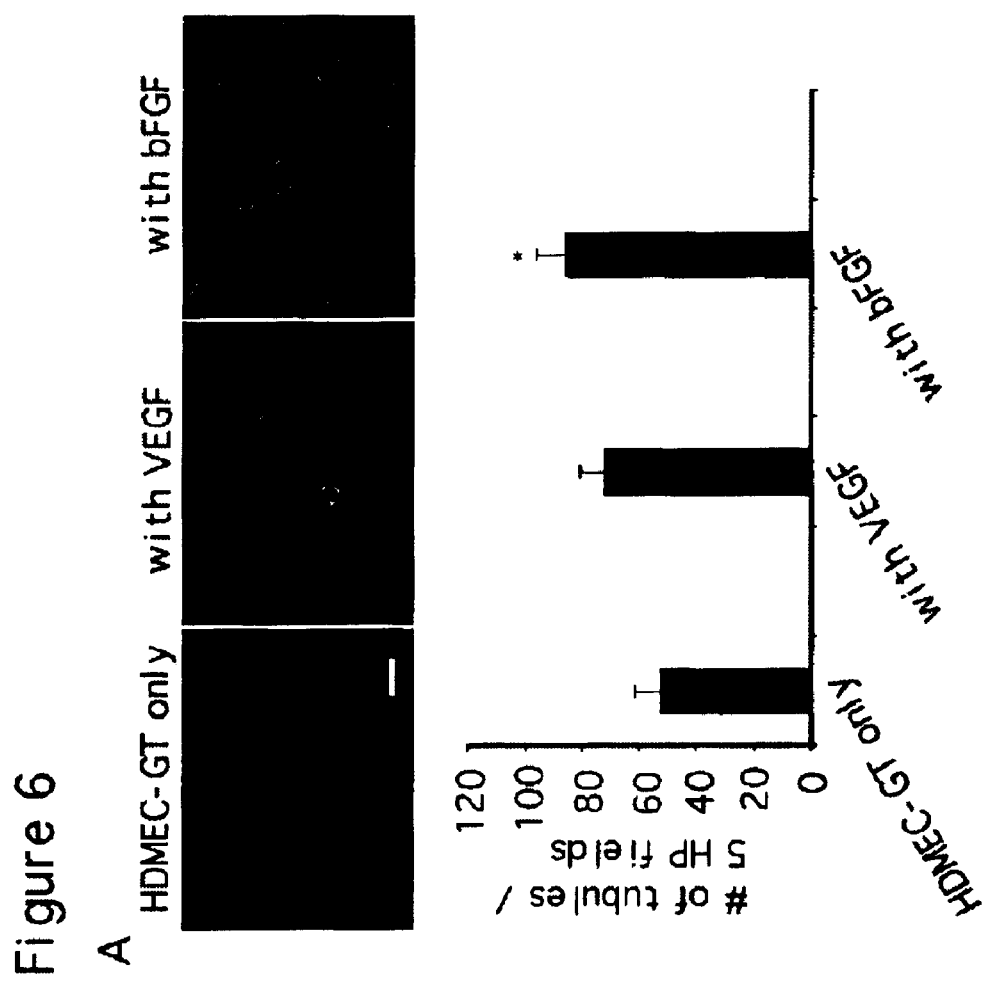
FIG. 6 shows the effect of pro- and anti-angiogenic factors on HDMEC-GT derived microvessels in vivo. (A) Human type IV collagen immunoreactive vascular lumens two weeks after implantation in the presence of VEGF (2 µg/ml) or FGF-2 (150 ng/ml) demonstrates increased vessel density within grafts. Quantification by micromorphometry shows increased vessels for both growth factors but only FGF-2 reached statistical significance (* p<0.01). Bar: ~20 µm. (B) Constitutive in vivo delivery of recombinant human endostatin (gel insert) via coincubation of HDMEC-GT and endostatin cDNA-transfected 293 cells in Matigel implants (HDMEC-GT+HEK293endo; b, d) shows decreased microvessel formation versus implants containing sham-transfected control cells (HDMEC-GT+HEK2931acZ; a, c) as demonstrated by both human type IV collagen staining (a, b) and binary images of eGFP fluorescence (c, d). Quantification by micromorphometry (left graph; n=6 different sections viewed) and total intensities extracted from binary images (Moss Filter™, right graph; n=6 different images for HEK2931acZ, n=8 different images for HEK293endo) shows inhibition is statistically significant (* p<0.001). Bar: ~20 µm.
Figure 6:
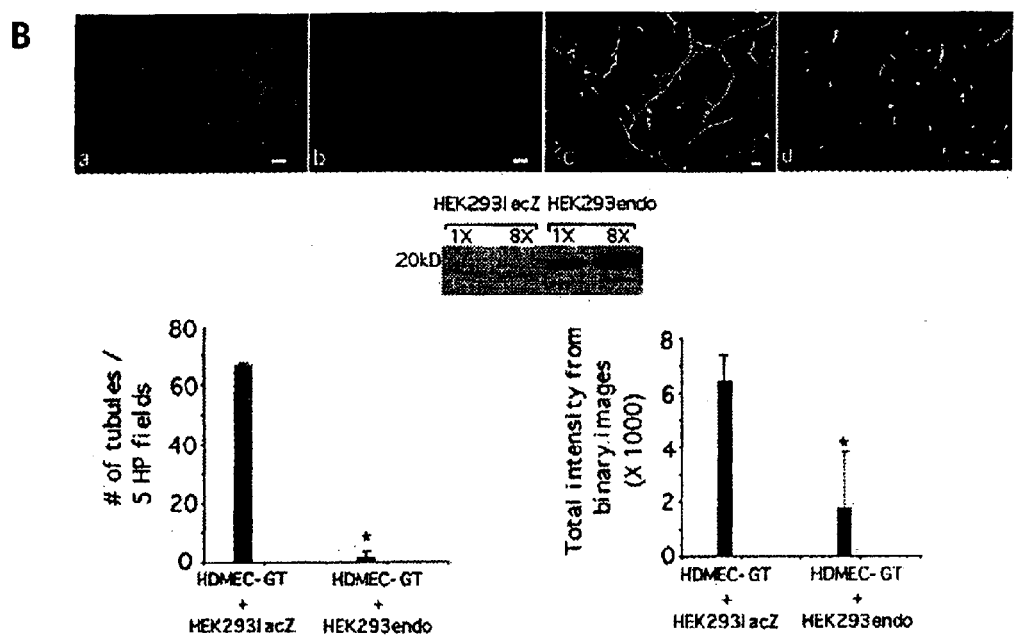

Matrigel implants were removed at 1, 2, 4 and 6 wk following xenografting, fixed in 10% buffered formalin overnight, paraffin-embedded and sectioned. H&E stained thin sections were prepared at Pan-insular Histopathology laboratory (Los Gatos, Calif.). For immunofluoresence, thin sections were deparaffinized and antigens retrieved in 10 mM citric acid (pH 6.0) by microwaving sections for 2×7 min. Sections were then incubated with anti-human type IV collagen IgG (Sigma, St. Louis, Mo.) primary antibody, followed by washing and Cy-3 conjugated secondary IgG according to standard protocols. Immunoreactive human collagen type IV signals were evident as annular and linear structures in all sections containing HDMEC versus both control IgG and sections from implants that did not contain human EC. Implants without FGF-2 or HDMEC contained little or no host microvessels, whereas, marked host vessel invasion was observed in the presence of FGF-2 alone[41]. For micromorphometry, 5 separate 20× fields were randomly selected per tissue section and the number of annular structures were counted and averaged. Unless specifically stated otherwise, 3 different sections were viewed per implant and replicate implants were grafted for each experimental condition (FIGS. 3 and 6).

For digital analysis of eGFP fluorescence images we used a novel algorithm (Moss Filter™) to determine the total amount of vascularization in each implant section. This filter determines whether or not each pixel is part of the fluorescently-labeled vascular region. The filter converts the original (8-bit) digital image into a binary image. Pixel values equal to 1 indicate vascularization, whereas zero values indicate no vascularization. The total amount of vascularization in each implant section is obtained by summing all the values in the binary image.

The filter converts the original array of pixel intensities into a new array, called the Discriminant, whose elements describe the likelihood that a particular pixel is part of the vascularized region. For each pixel in the original image, we calculate an element of the Discriminant array. We write:

Element of Discriminant array=$\Sigma_{(row\ and\ column)}$–(Pixel Intensity–Background)*(Local Curvature)/(|Local Slope|+E where E (a small number) ensures a nonzero denominator. The local curvature and local slope are the second and first derivatives, which are calculated along a row or column for each member of the pixel intensity array. The Discriminant selects locally for a high, peaked, and/or plateaued region ("mountain top"), which is the topological structure of the pixel intensities of the fluorescently-labeled vascular network. The user specifies only a single background pixel intensity and a single numerical threshold for the computed discriminant (how much of a mountain top is desired) for each image. An initial binary image is constructed from all discriminant values that exceed this threshold value. This binary image is refined further by retaining only those pixels that have a value of 1 and have at least two nearest neighbors (each pixel has 8 neighbors) that also have a value of 1. This represents a minimum requirement for connectivity. From this binary, we retain only those pixels that have a value of 1 and have at least three nonzero nearest neighbors. The final binary image is obtained by removing all isolated nonzero valued pixels. FIGS. 3A (Bin) and 6.B show representative binary images of the original TIFFs.

Intravascular Tracer Experiments

Mice containing HDMEC-GT xenografts two weeks after implantation were injected with 1.0 μm diameter red fluorescent microspheres (Molecular Probes, Eugene, Oreg.) via tail vein cannulation. After approximately 1 minute, implants were removed and tissues processed as described above for thick section whole mounts. FITC and rhodamine filters were used to visualize eGFP and red microspheres, respectively, and images were captured using either the Zeiss Axioskope or Gen II Multi-dimensional Imager, a fully automated inverted high speed imaging station powered by Universal Imaging Corporation Metamorph™ software.

Endostatin Blocking Experiments

Inhibition of in vivo vessel formation by local delivery of human endostatin was accomplished as follows: The plasmid pGT60hEndo, expressing recombinant human endostatin (InvivoGen, San Diego, Calif.), was stably transfected into human embryonic kidney (HEK293) cell line by calcium phosphate transfection (Invitrogen, Carlsbad, Calif.). Western blot of culture media using endostatin-specific IgG (kind gift from Rupert Timpl, Max Plank Institute, Martinsreid, Germany) showed expression of a 22kD protein in HEK293endo only. HEK293 cells expressing lacZ served as a control for both Western blots and grafting experiments. The cell implantation procedure was the same as that described above except that 1×10$^5$ (or 10$^4$ or 10$^3$) transfected HEK were mixed with HDMEC-GT immediately prior to implantation. Grafts were examined at both one week and two after injection and sections were analyzed by both micromorphometry and eGFP as previously described.

Creation of eGFP-Labeled, Telomerized HDMEC

Our previous studies showed that ectopic expression of recombinant hTERT reconstituted telomerase activity efficiently in human dermal microvascular EC (HDMEC) derived from neonatal foreskin[21]. In the present study, we used both a previously characterized telomerized HDMEC population (HDMEC-T) and a new EC line produced by co-transduction of eGFP and hTERT into HDMEC, called HDMEC-GT. The parental cells used for creating HDMEC-GT were also transduced with eGFP (HDMEC-G). As shown by the TRAP ladder assay, both telomerized EC lines (HDMEC-T and HDMEC-GT) exhibited high telomerase activity, whereas, mid passage parental primary HDMEC (HDMEC, PD25; HDMEC-G, PD28) showed little or no activity. A mass culture of HDMEC-GT with ~100% eGFP positively was then produced by FAC sorting (FIG. 1B). The phenotypic and functional properties of this HDMEC-GT subpopulation in vitro were identical to HDMEC-T and both cell populations formed relatively slow growing epitheliod monolayers that expressed all EC markers, including TNF∂-inducible ICAM, VCAM and E-selectin.

In vitro Tubule Formation

Figure 2:
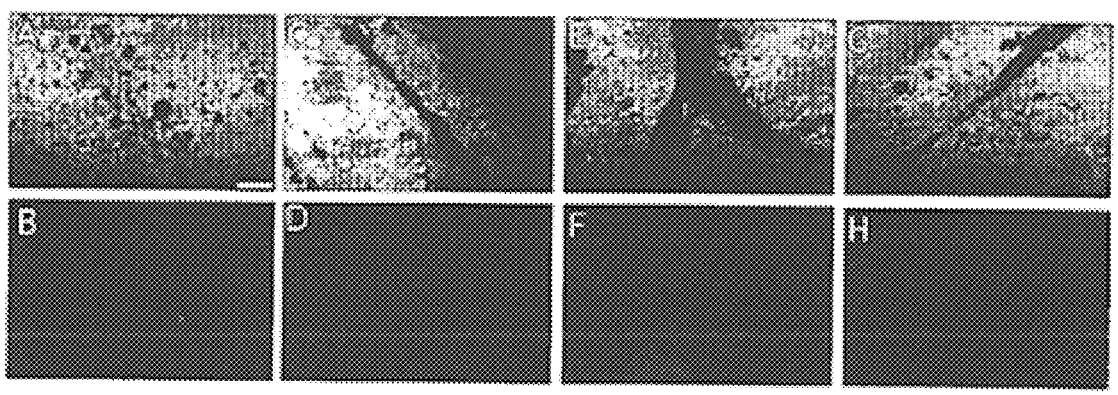
FIG. 2 shows the In vitro tubule formation in primary and telomerized HDMEC using 3D Matrigel. Phase contrast (A, C, E, G) and fluorescence (B, D, F, H) microscopy showed tubule formation was inversely correlated with in vitro aging of primary cells. Pre-senescent primary cells (HDMEC-G, PD38, A & B) exhibited no tubules and mid passage HDMEC-G (PD20, C & D) formed nonbranched, linear structures with diminished GFP fluorescence. HDMEC-GT (PD56, E-H) formed mature tubules with many branches and strong GFP signal (E, F, G, H). Bar: ~20 µm.

The functionality of HDMEC-GT was also assessed by tracking morphogenetic movements of cells in a "permissive" matrix environment in vitro. As shown in FIG. 2 the formation of tubule structures in 3D Matrigel using both parental primary cells and HDMEC-GT was visualized by phase contrast and fluorescence microscopy. Similar to pre-senescent primary human umbilical vein endothelial cells (HUVEC) seeded atop Matrigel[21] we found that pre-senescent primary HDMEC-G (PD38) did not form tubules in 3-D Matrigel (FIGS. 2A, 2B) but mid-passage (PD20) HDMEC-G did. However, we noted that both the number and branching of HDMEC-G tubule structures were diminished (FIGS. 2C, 2D) relative to HDMEC-GT which formed tubules with strong eGFP signals (FIGS. 2F, 2H) and abundant branching (FIGS. 2E, 2G). HDMEC-GT were used at twice the replicative age (PD56) of senescent primary cells (~PD25–30). These results suggest that telomerized, eGFP-labeled HDMEC may have an advantage in forming genetically-tagged vascular structures in vivo.

Persistence of Telomerized EC in vivo

We subcutaneously implanted both HDMEC-GT and in vitro aged HDMEC as 3D Matrigel xenografts in SCID mice and analyzed the grafts at 2, 4 and 6 wk after implantation. FIG. 3A shows representative H&E, eGFP fluorescent images and digitized fluorescent images (Bin) of HDMEC (PD38) and HDMEC-GT (PD56) 2 weeks after xenografting. While H & E staining did not reveal major differences, both grafts showed some areas containing cystic spaces and lymphocyte infiltration and other areas where clear endothelial-lined spaces containing red blood cells were evident. Direct immunofluorescence microscopy using anti-human type IV collagen immunoreactivity in thin sections revealed bright circular and linear structures in the HDMEC-GT-containing implants, but not in implants containing PD38 parental cells (FIG. 3A, Co14 images). Combined with the H&E results, this suggested that the implants contained a mixture of both host murine and human vessels. The human origin of these structures was confirmed by fluorescence microscopy of implant thick sections that showed bright green tubular structures in HDMEC-GT grafts (FIG. 3A, GFP images). We also used a digital image program (Moss Filter™) to enhance visualization of these fluorescent vessels (FIG. 3A, Bin). eGFP expression correlated well with Co14 immunoreactivity in young primary HDMEC-G (PD<15) and HDMEC-GT independent of PD; however, we noted that eGFP fluorescence signal intensity was inversely correlated with PD in primary cells. Thus, in vitro aged HDMEC-G had weaker eGFP signals relative to HDMEC-GT (e.g. FIG. 2C, D vs. E-H). These results were consistent in multiple different experiments using over 50 mice, each with up to three implants.

Because primary HDMEC-G did not maintain eGFP fluorescence with time we used micromorphometry of anti-human type IV collagen immunoreactivity (counting lumenal/circular structures per 5 high power fields in thin sections) to quantify human vessel density in the implants from both primary and telomerized EC. FIG. 3B shows that while both mid (PD20, M) and late (PD40, L) passage primary HDMEC exhibited decreased vessel density with time after implantation, telomerized vessels were maintained at about the level of early passage (PD12, E) primary cells. Due to the lack of sufficient numbers of the latter cells we were unable to test the long-term survival of early passage parental primary cells in vivo. However, mid- and late-passage parental HDMEC showed statistically significant lower vessel densities relative to that of telomerized HDMEC implants, ($p<0.01$ and $p<0.001$, respectively. $n=3$ each).

In vivo Vessel Formation is EC Specific

Figure 4:
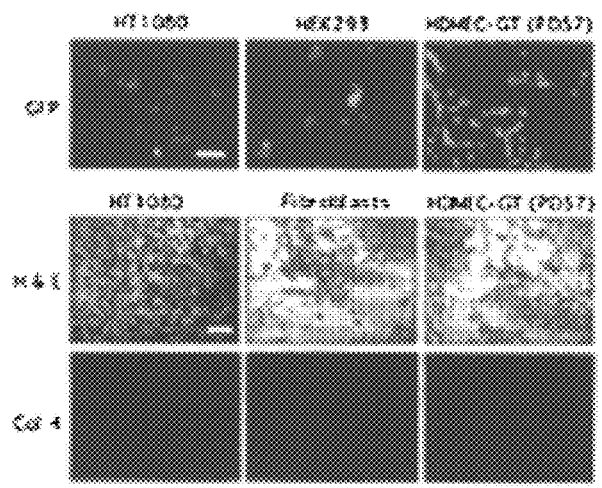
FIG. 4 shows the specificity of HDMEC-GT at forming in vivo tubules in SCID mice. Upper panels, eGFP-transduced HT1080 and 293 embryonic kidney tumor cells formed fluorescent tumor masses 2 weeks after implantation in Matigel, whereas, HDMEC-GT formed microvascular networks only. Lower panels, H&E staining and immunofluorescence of Matrigel implanted HT1080 cells, human dermal fibroblasts and HDMEC-GT show human type IV collagen immunoreactive lumenal structures present only in HDMEC-GT. Bar: ~20 µm.

To prove that formation of these human vessel structures in SCID mouse xenografts was a property of EC but not other cells, human fibrosarcoma cells (HT1080), embryonic kidney (HEK293) cells, or primary human dermal fibroblasts were xenografted in duplicate animals under identical conditions as telomerized HDMEC in SCID mice. Two weeks after implantation of eGFP-transduced tumor cells, sections of implants showed HDMEC-GT formed tubular networks while HT1080 and HEK293 formed solid, fluorescent tumor masses (FIG. 4, upper panel). Type IV collagen immunoreactivity showed no evidence of lumenal structures in HT1080 or fibroblast implants (FIG. 4, lower panels).

Recent demonstrations of vascular mimicry using melanoma cells in vitro and in vivo suggests that while EC may not be the only cell type capable of forming vascular structures[22,23] we show the absolute requirement for human EC in our in vivo model of human vessel formation. However, since FIG. 2 showed that tubule structures could be formed in 3D Matrigel in vitro without implantation in SCID mice, we determined whether these capillary structures formed in vivo could function as living blood vessels in SCID mice.

Figure 5:
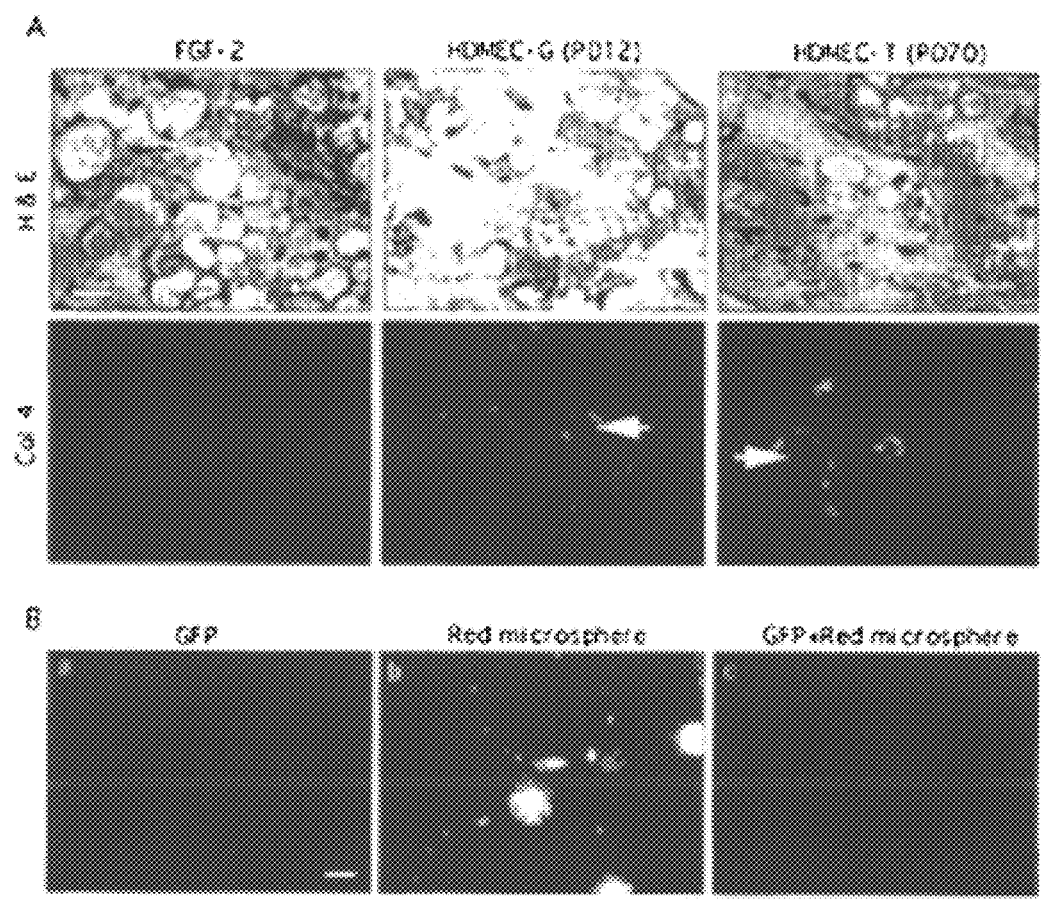
FIG. 5 shows telomerized human microvessels communicate with host murine circulatory system. (A) Red blood cells (arrows) are visible within human type IV collagen immunoreactive lumenal structures derived from both young primary HDMEC-G (PD12) and telomerized HDMEC-T (PD70). Host vessel invasion of Matrigel implants is stimulated in the presence of FGF-2 (upper left panel); however, H & E staining, does not differentiate human from host vessels (middle and right upper panels). Human basement membrane collagen reproducibly reacts with human microvessels in Matrigel (middle and right lower panels). Bar: ~10 µm. (B) Intravenous injection of red microspheres results in appearance of red tracer within eGFP(+) vessels. Dual scans using FITC (a) and rhodamine fluorescence (b) of the same image shows overlap of signals in some vasculature. Host vessels containing red tracer are present in the same field. In (c), FITC and rhodamine signals were overlaid (Metamorph, UIC) to simultaneously demonstrate the presence of tracer beads within eGFP(+) branched vessel. Bar: ~20 µm.

Functional human vessels carry host mouse blood. Previous work has shown that an angiogenic factor (e.g. FGF-2) incorporated into Matrigel implants in SCID mice was sufficient to allow invasion of host murine blood vessels[24]. FIG. 5A demonstrates this effect in the absence of human EC (upper left panel). However whenever human HDMEC (primary or telomerized) were engrafted in SCID mice as Matrigel implants in the absence of FGF-2, we found anti-human type IV collagen immunoreactive vascular structures that contained lumenal red blood cells (FIG. 5 upper middle and right panels). Given that type IV collagen immunoreactivity associates with eGFP flourescence (FIGS. 3, 4), the appearance of host blood cells within these vessels strongly suggests that anastomoses have formed between human and mouse vessels. However, it is possible that post-mortem surgical manipulation of implants may have resulted in artifactual contamination or spillage of blood across tissue sections.

To demonstrate functional murine-human vessel communication we directly delivered an intravascular tracer (red fluorescence microspheres) into the host circulation via tail vein cannulation and found that the tracer localized within eGFP-labeled, human vascular structures one minute after injection (FIG. 5B). The proportion of human vessels that contained the tracer varied between approximately 5% to 50% of total eGFP-labeled vessels in multiple experiments.

The majority of implants showed host vessels contained varying amounts of the tracer. Red signals adjacent to eGFP-labeled vessels (FIG. 5B, panel b) suggested that vascular leakage from these newly formed human vessels had occurred. Since we initially examined host-human vessel communication at two weeks after EC implantation, it is likely that the leakage phenomenon may be different at later time points, as vessels 'mature' in vivo. Recent studies indicate that murine-human chimeric microvessels are detectable within one month of xenografting primary human EC over-expressing bcl-2 in SCID mice and it is possible that host perivascular support cells (i.e. pericytes) contribute to stabilization of human vessels thereby decreasing vascular leakage at later time points[3].

These results support and extend our previous in vitro studies that showed a survival advantage of HDMEC-T relative to aged primary HDMEC[21]. Although telomerase life-extended cells have been used recently to engineer functional tissues in vivo[25,26], here we show that telomerized human blood vessels can be grown in SCID mice and communicate with the host circulatory system. Furthermore, by directly comparing in vitro-aged primary parental EC to HDMEC-T our results demonstrate for the first time that telomerase activation in human EC results in the maintenance of a stable microvascular phenotype in vivo. Importantly, implanted telomerized EC did not result in tumor formation up to six weeks after implantation, consistent with previous studies of hTERT-transduced primary cells[21,27,28].

Since HDMEC-T,were originally isolated from neonatal dermal microvessels, then dispersed cells allowed to reform vascular structures within Matrigel implants, this SCID-human capillary blood vessel model appears to exhibit elements of both intussusception and vascular remodeling in vivo[29-31]. However, we have not demonstrated all known steps of angiogenesis nor characterized the angiogenic program of HDMEC-GT in vivo. While an intriguing possibility to consider, it remains to be shown whether a small subpopulation of bone marrow derived EC precursors (e.g. angioblasts), present in the neonatal HDMEC cultures we transduced with hTERT, could be contributing a 'vasculogenic' response in this model system[31-35]. Characterizing and testing different FAC-sorted HDMEC-T populations using our in vivo system may help to clarify potential involvement of such EC precursor populations.

In vivo Vessel Density Correlates with Pro-Angiogenic and Angiostatic Factors

In vivo angiogenesis models have been continuously developed during the past 30 years[4,24]. Most of these models evaluate new blood vessel formation based on the growth of host animal capillaries in response to a controlled microenvironment. More recently, normal human tissue or cancer cell lines have been xenografted in SCID mice for studies of would healing and tumors[36,37]. In order to test whether HDMEC-T-derived microvascular networks could be modulated by known pro-angiogenic factors, VEGF or FGF-2 were mixed with cells and Matrigel before implantation. Using human type IV collagen micromorphometry, we found statistically increased human vessel density two weeks after grafting HDMEC-GT with FGF-2 (FIG. 6.A). While VEGF showed a 20–30% increased vessel density relative to controls, micromorphometry did not demonstrate statistical significance.

To test the effect of potential angiogenic blocking agents in this model, a 1:10 ratio of 293 cells expressing endostatin cDNA (HEK293endo) was mixed with HDMEC-GT together with Matrigel immediately before implanting in SCID mice. Implants removed after both one and two weeks demonstrated dispersed, fluorescent spindle-shaped and round cells in grafts from endostatin tissue versus sham transfected (293HEKlacZ) controls (FIG. 6.B;-d vs. c). Morphometric analysis and digital quantification using total fluorescence intensity extracted from binary images (FIG. 6.B lower bar graphs) demonstrated statistically significant loss of vessel density in HEK293endo implants, confirming the morphologic appearance of these tissues.

In summary, we have established a system for studying the mechanisms of human microvessel formation in a controlled experimental setting in vivo. Our model relies on the superior survival and uniformity of HDMEC-GT, is specific and quantitative. Telomerized, genetically-tagged human EC respond appropriately to both pro-angiogenic and angiostatic factors by modulating vessel density in vivo. While we reported that our telomerized EC populations resist apoptotic induction relative only to in vitro aged primary parental EC populations[21] the potential for altered apoptotic signaling in telomerized EC lines in vivo may impact the ability of our model to mimic the exact responses of primary HDMEC and/or dermal capillaries in human tissues. Nevertheless, this system does not depend on constitutive blockade of apoptotic signal transduction pathways via enforced bcl-2 expression[2,3] and thus it provides a superior platform for testing the effects of agents that may modulate EC programmed cell death. Such characteristics are required for preclinical drug screening programs and our model may be utilized in the design of engineered human vascular tissues that will facilitate surgical grafting, vascular implantation, chronic wound management and clarification of tumor angiogenesis[33,34].

REFERENCES

The following references are hereby incorporated by reference in their entirety.

1. L'Heureux N., Paquet S., Labbe R., Germain L. & Auger F. A. A completely biological tissue-engineered human blood vessel. *FASEB J.* 12, 47–56 (1998).
2. Nör, J., Joan, C., Mooney, D. & Polverini, P. Vascular Endothelial Growth Factor (VEGF)—Mediated Angiogenesis is Associated With Enhanced Endothelial Cell Survival and induction of Bcl-2 Expression. *Am. J. Pathol.* 154, 375–384 (1999).
3. Schechner, J. et al. In vivo formation of complex microvessels lined by human endothelial cells in an immunodeficient mouse. *Proc. Natl. Acad. Sci USA.* 97, 9191–9196 (2000).
4. Jain, R. K., Schlenger, K., Höckel, M. & Yuan, F. Quantitative angiogenesis assays: progress and problems. *Nat. Med.* 3, 1203–1208 (1997).
5. Palmer, R., Ferrige, A. & Moncada, S. Nitric Oxide release accounts for the biological activity of EDRF. *Nature* 327, 524–526 (1987).
6. Pili, R. et al. Altered angiogenesis underlying age-dependent changes in tumor growth. *J. Natl. Cancer Inst.* 86, 1303–1314 (1994).
7. Reed, M. J., Corsa, A. C., Kudravi, S. A., McCormick, R. S. & Arthur, W. T. A deficit in collagenase activity contributes to impaired migration of aged microvascular endothelial cells. *J. Cellular Biochem.* 77, 116–126 (2000).
8. Rivard, A. et al. Age-dependent impairment of angiogenesis. *Circulation* 99, 111–120 (1999).
9. Swift, M. E., Kleinman, H. K. & DiPietro, L. A. Impaired wound repair and delayed angiogenesis in aged mice. *Lab. Invest.* 79, 1479–1487 (1999).
10. Whikehart, D. R., Register, S. J., Chang, Q. & Montgomery, B. Relationship of telomeres and p53 in aging bovine corneal endothelial cell cultures. *Invest. Ophthal. & Vis. Sci.* 41, 1070–1075 (2000).
11. Chang, E. & Harley, C. B. Telomere length and replicative aging in human vascular tissues. *Proc. Natl. Acad. Sci USA.* 92, 11190–11194 (1995).
12. Maier, J. A., Voulalas, P., Roeder, D. & Maciag, T. Extension of the life-span of human endothelial cells by an interleukin-1 alpha antisense oligomer. *Science* 249, 1570–1574 (1990).
13. Watanabe, Y., Lee, S. W., Detmar, M., Ajioka, I. & Dvorak, H. F. Vascular permeability factor/vascular endothelial growth factor (VPF/VEGF) delays and induces escape from senescence in human dermal microvascular endothelial cells. *Oncogene* 14, 2025–2032 (1997).
14. Shelton, D. N., Chang, E., Whittier, P. S., Choi, D. & Funk, W. D. Microarray nalysis of replicative senescence. *Cur. Biol.* 9, 939–945 (1999).
15. Ades, E. W. et al HMEC-1 Establishment of an Immortalized Human Microvascular Endothelial Cell Line. *J. Invest. Dermatol.* 99, 683–690 (1992).
16. Dubois, N. A., Kolpack, L. C., Wang, R., Azizkhan, R. G. & Bautch, V. L. Isolation and characterization of an established endothelial cell line from transgenic mouse hemangiomas. *Exp. Cell Res.* 196, 302–313 (1991).
17. Candal, F. J. et al. BMEC-1: a human bone marrow microvascular endothelial cell line with primary cell characteristics. *Microvasc. Res.* 52, 221–234 (1996).
18. Fontijn, R. et al. Maintenance of vascular endothelial cell-specific properties after immortalization with an amphotrophic replication-deficient retrovirus containing human papilloma virus 16 E6/E7 DNA. *Exp. Cell Res.* 216, 199–207 (1995).
19. Cockerill, G. W., Meyer, G., Noack, L., Vadas, M. A. & Gamble, J. R. Characterization of a spontaneously transformed human endothelial cell line. *Lab. Invest.* 71, 497–509 (1994).
20. Rhim, J. S. et al. A human vascular endothelial cell model to study angiogenesis and tumorigenesis. *Carcinogenesis* 19, 673–681 (1998).
21. Yang, J. et al Human endothelial cell life extension by telomerase expression. *J. Biol. Chem.* 274, 26141–26148 (1999).
22. Maniotis, A. J. et al. Vascular channel formation by human melanoma cells in vivo and in vitro: vasculogenic mimicry. *Am. J. Pathol.* 155, 739–752 (1999).
23. Folberg, R., Hendrix, M. J. & Maniotis, A. J. Vasculogenic mimicry and tumor angiogenesis. *Am. J. Pathol.* 156, 361–81 (2000).
24. Capogrossi, M. C. & Passaniti, A. An in vivo angiogenesis assay to study positive and negative regulators of neovascularization. *Methods in Molecular Medicine* (1998).
25. Shay, J. W. & Wright, W. E. The use of telomerized cells for tissue engineering. *Nat. Biotechnol.* 18, 22–23 (2000).
26. Thomas, M., Yang, L. & Hornsby, P. J. Formation of functional tissue from transplanted adrenocortical cells expressing telomerase reverse transcriptase. *Nat. Biotechnol.* 18, 39–42 (2000).
27. Jiang, X. et al. Telomerase expression in human somatic cells does not induce changes associated with a transformed phenotype. *Nat. Genet.* 21, 111–114 (1999).

28. Morales, C. et al Absence of cancer-associated changes in human fibroblasts immortalized with telomerase. *Nat. Genet.* 21, 115–118 (1999).
29. Carmeliet, P. Mechanisms of angiogenesis and arteriogenesis. *Nat. Med.* 6, 389–395 (2000).
30. Helmlinger, G., Endo, M., Ferrara, N;, Hlatky, L. & Jain, R. K. Growth factors: formation of endothelial cell networks. *Nature* 405, 139–141 (2000).
31. Risau, W. Mechanisms of angiogenesis. *Nature* 386, 671–674 (1997).
Asahara T. et al. Isolation of putative progenitor endothelial cells for angiogenesis. *Science* 275, 964–967 (1997).
Shi, Q. et al. Evidence for Circulating Bone Marrow-Derived Endothelial Cells. *Blood* 92, 362–367 (1998).
Takahashi, T. et al. Ischemia- and cytokine-induced mobilization of bone marrow-derived endothelial progenitor cells for neovascularization. *Nat. Med.* 5, 434–438 (1999).
Kalka, C. et al Transplantation of ex vivo expanded endothelial progenitor cells for therapeutic neovascularization. *Proc. Natl. Acad. Sci USA*. 97, 3422–3427 (2000).
36. Christofidou-Solomidou, M., Bridges, M., Murphy, G. F., Albelda, S. M. & DeLisser, H. M. Expression and function of endothelial cell alpha v integrin receptors in wound-induced human angiogenesis in human skin/SCID mice chimeras. *Am. J. Pathol.* 151, 975–983 (1997).
37. Yuan, F. et al. Time-dependent vascular regression and permeability changes in established human tumor xenografts induced by an anti-vascular endothelial growth factor/vascular permeability factor antibody. *Proc. Natl. Acad. Sci USA*. 93, 14765–14770 (1996).
38. Normand, J. & Karasek, M. A. A method for the isolation and serial propagation of keratinocytes, endothelial cells, and fibroblasts from a single punch biopsy of human skin. *In Vitro Cellular & Dev. Biol. Animal* 31, 447–455 (1995).
39. Romero, L. I., Zhang, D. N., Herron, G. S. & Karasek, M. A. Interleukin-1 induces major phenotypic changes in human skin microvascular endothelial cells. *J. Cellular Physiol.* 173, 84–92 (1997).
40. Kinsella, T. M. & Nolan, G. P. Episomal vectors rapidly and stably produce high-titer recombinant retrovirus. *Hum. Gene Ther.* 7, 1405–1413 (1996).
41. Passaniti, A. et al. A simple, quantitative method for assessing angiogenesis and antiangiogenic agents using reconstituted basement membrane, heparin, and fibroblast growth factor. *Lab. Invest.* 67, 519–528 (1992).

What is claimed is:

1. An in vivo assay system for determining the effect of a pharmaceutically acceptable compound on angiogenesis comprising:
   a. A composition of human endothelial cells; and
   b. A non-human, inmuno-compromised host, wherein said cells have a recombinant expression cassette encoding telomerase.

2. The in vivo assay system of claim 1 further comprising a digital imaging device.

3. The in vivo assay system of claim 2 wherein said device detects fluorescence.

4. The in vivo assay system of claim 1 wherein said cells express a genetic marker.

5. The in vivo assay system of claim 4 wherein said genetic marker is enhanced green fluorescent protein (eGEP).

6. The in vivo assay system of claim 1 wherein said telomerase is a human telomerase reverse transcriptase catalytic subunit.

7. The in vivo assay system of claim 1 wherein said host is a SCID mouse.

8. The in vivo assay system of claim 1 wherein said compound is selected from the group consisting of growth factors, extracellular matrix molecules, proteinase inhibitors, cell adhesion molecules, angiostatic factors, apoptotic inducers, and inflammatory mediators.

9. The in vivo assay system of claim 8 wherein said compound is a growth factor.

10. The in vivo assay system of claim 9 wherein said growth factor is selected from the group consisting of angiopoietins, CTGF, EGF, FGF-2, IGF, PLGF, PDGF, SF, TGF, and VEGF.

11. The in vivo assay system of claim 10 wherein said growth factor is VEGF.

12. The in vivo assay system of claim 10 wherein said growth factor is FGF-2.

13. The in vivo assay system of claim 1 wherein said compound is capable of modulating tumor angiogenesis.

14. An in vivo method for analyzing the effect of a pharmaceutically acceptable compound on angiogenesis comprising:
   a. providing a composition comprising human endothelial cells, wherein said cells have a recombinant expression cassette encoding telomerase and a genetic marker;
   b. adding a compound to said composition;
   c. implanting said composition in a non-human, immunocompromised host; and
   d. determining the amount of angiogenesis in the implanted cells by measuring the expression of said transformed genetic marker.

15. The in vivo method of claim 14 wherein said telomerase is a human telomerase reverse transcriptase catalytic subunit.

16. The in vivo method of claim 14 wherein said genetic marker is enhanced green fluorescent protein (eGFP).

17. The in vivo method of claim 14 wherein expression of said genetic marker is detected by a digital imaging device.

18. The in vivo method of claim 14 wherein said compound is selected from the group consisting of growth factors, extracellular matrix molecules, proteinase inhibitors, cell adhesion molecules, angiostatic factors, apoptotic inducers, and inflammatory mediators.

19. The in vivo method of claim 18 wherein said compound is a growth factor.

20. The in vivo method of claim 19 wherein said compound is VEGF.

21. The in vivo method of claim 19 wherein said compound is FGF-2.

22. The in vivo method of claim 14 wherein said composition further comprises matrigel.

23. The in vivo method of claim 14 wherein said host is a SCID mouse.

24. The in vivo method of claim 14 wherein said compound is capable of modulating tumor angiogenesis.

25. A non-human, immuno-compromised host comprising at least one capillary, venule or arteriole formed from a composition of human endothelial cells having a recombinant expression cassette encoding telomerase, and a genetic marker, wherein blood of said host is transmitted through said at least one capillary, venule or arteriole.

26. The non-human immuno-compromised host of claim 25 wherein said host is a SCID mouse.

27. The non-human immuno-compromised host of claim 25 wherein said telomerase is a human telomerase reverse transcriptase catalytic subunit.

28. The non-human immuno-compromised host of claim 25 wherein said genetic marker is enhanced green fluorescent protein (eGFP).

* * * * *

UNITED STATES PATENT AND TRADEMARK OFFICE
CERTIFICATE OF CORRECTION

PATENT NO. : 6,906,237 B2  
DATED : June 14, 2005  
INVENTOR(S) : G. Scott Herron It is certified that error appears in the above-identified patent and that said Letters Patent is hereby corrected as shown below:

Title page,
Item [54], Title, please replace "VIVO" with -- IN VIVO --.

Column 15,
Line 59, please replace "inmuno" with -- immuno --.

Column 16,
Line 3, please replace "(eGEP)" with -- (eGFP) --.

Signed and Sealed this

Sixth Day of September, 2005

JON W. DUDAS  
*Director of the United States Patent and Trademark Office*